United States Patent [19]

Shimada

[11] Patent Number: 4,507,564
[45] Date of Patent: Mar. 26, 1985

[54] SURFACE DEFECT DETECTING APPARATUS

[75] Inventor: Masayoshi Shimada, Kawasaki, Japan

[73] Assignee: Tokyo Shibaura Denki Kabushiki Kaisha, Kawasaki, Japan

[21] Appl. No.: 594,430

[22] Filed: Mar. 29, 1984

Related U.S. Application Data

[63] Continuation of Ser. No. 306,238, Sep. 28, 1981.

[30] Foreign Application Priority Data

Sep. 27, 1980 [JP] Japan .................. 55-137391[U]

[51] Int. Cl.$^3$ .......................................... G01N 21/89
[52] U.S. Cl. ................................. 250/563; 356/431
[58] Field of Search ......................... 250/562-563, 250/571 ≧ 572; 356/237-239, 430-431; 358/106

[56] References Cited

U.S. PATENT DOCUMENTS

| | | | |
|---|---|---|---|
| 4,134,684 | 1/1979 | Jette | 250/563 X |
| 4,223,346 | 9/1980 | Neiheisel et al. | 356/237 X |
| 4,240,110 | 12/1980 | Henry | 358/106 X |
| 4,327,375 | 4/1982 | Leclerc | 358/106 X |

OTHER PUBLICATIONS

Mayes et al., "High-Speed Image Capture for Mechanical Analysis", IBM Technical Disclosure Bulletin, vol. 16, No. 7, Dec. 1973, pp. 2169-2171.

Primary Examiner—Edward P. Westin
Attorney, Agent, or Firm—Oblon, Fisher, Spivak, McClelland & Maier

[57] ABSTRACT

Disclosed is a surface defect detecting apparatus comprising a scanning device for scanning a rolled steel plate rolled and transferred by a pair of rolls at a fixed period over its full width to successively produce signals representing a surface condition of the rolled steel plate over the full width thereof, and a defect signal generating circuit for producing output signals representing the presence of a surface defect on the surface of the rolled steel plate in accordance with output signals from the scanning device. The surface defect detecting apparatus is further provided with a pulse generator for producing pulses every rotation of the roll, a memory, a display unit, and a control system which responds to output pulses from the pulse generator to sequentially write defect signals generated from the defect signal generation circuit into the memory, reads out the data from the memory after the memory is full up with the data, and causes the display unit to display on one line the data obtained every rotation of the roller.

2 Claims, 4 Drawing Figures

FIG. 2

| A(11) | A(12) | ---------------- | A(1N) |
|-------|-------|------------------|-------|
| A(21) | A(22) | ---------------- | A(2N) |
| A(31) | A(32) | ---------------- | A(3N) |
|       |       |                  |       |
| A(M1) | A(M2) | ---------------- | A(MN) |

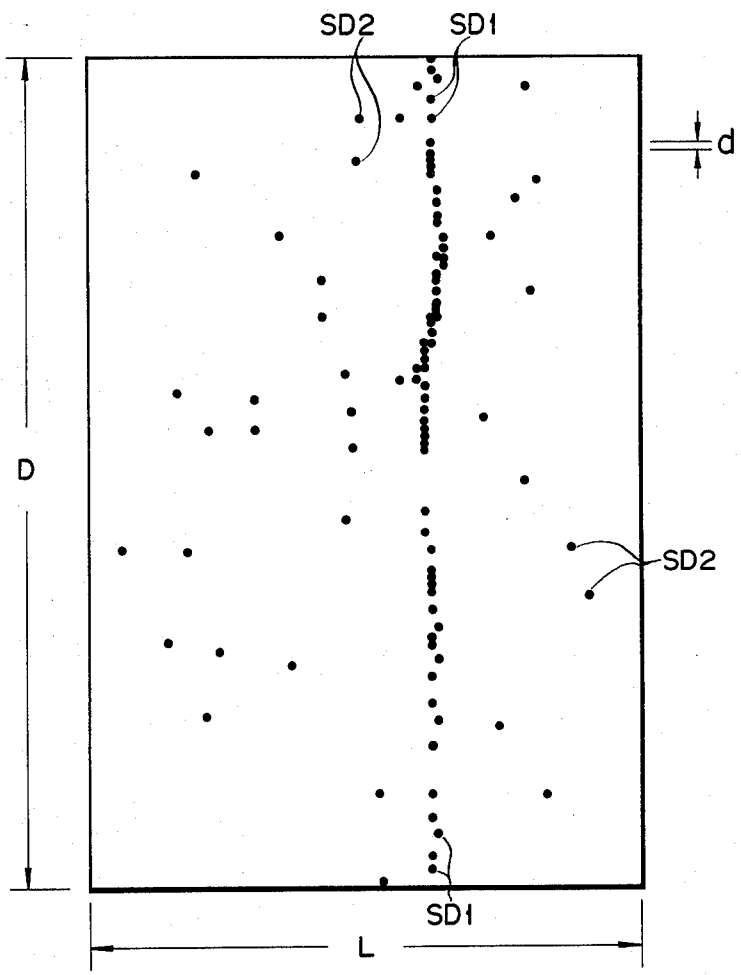

SURFACE DEFECT DETECTING APPARATUS

This application is a continuation of application Ser. No. 306,238, filed Sept. 28, 1981.

BACKGROUND OF THE INVENTION

The present invention relates to a surface defect detecting apparatus for detecting a surface condition of an object to be checked such as a steel plate rolled by rolls.

Conventionally, it is known that rolled steel plates are made by a hot rolling or a cold rolling. Usually, surface defects made on the rolled steel plate may be divided into two types, one including scabs and scales which are caused by the property of the steel plate itself and the other including scars and the like which are made by the rolls in a rolling step, and these surface defects appear on the steel plate at random. Since, in particular, surface defects made on the steel plate by printing the scar or the like on the roll surface will appear periodically, the quality of the steel is remarkedly lowered. In practice, it has taken a relatively long time to detect the surface defect on the steel plate and stop the rolls so that a large amount of steel plate may be rolled uselessly. Therefore, it is required to check whether the roll itself has any defect or not and replace the roll without delay, if necessary. A surface defect detecting apparatus has been proposed which finds out a defect on the roll by inspecting a surface condition of the rolled steel plate on the assumption that a defect of the roll, if any, should appear substantially periodically on the surface of the rolled steel plate. In an example of such a surface defect detecting apparatus, the surface of the rolled steel plate is scanned by light, and the light reflected from the rolled steel plate is converted into an electric signal by a photoelectric converting device. The level of an output signal from the photoelectric converting device is determined in a level determination circuit. For example, when a signal at a level lower than a predetermined level, or an electric signal obtained when a defected portion is scanned, is received, a "1" signal is produced from the level determination circuit. The output signal from the determination circuit is applied to a plurality of shift register circuits connected in a cascade fashion. Each shift register circuit includes shift registers with a number of stages enough to store all the logic signals that are generated from the determination circuit during one rotation of the roll. Further, an output terminal of the last stage shift register of each of these shift register circuits are connected to an input terminal of an AND gate. In this surface defect detecting apparatus, when the "1" signal is generated from the AND gate, it is judged that there is a defect on the roll. To be more specific, the judgment is based on an anticipation that, if there is any defect on the roll, the defect might periodically appear on the surface of the rolled steel plate and, therefore, the "1" signal indicating the presence of the defect on the rolled steel plate is stored in the same digit position, for example, in the last stage register of each shift register circuit, with the result that the "1" signal is generated from the AND gate. As a matter of fact, a slip occurs between the roll and the rolled steel plate and the steel plate may be stretched or contracted, a distance of the rolled steel plate transferred for each rotation of the roll is not constant. Therefore, the defects which appear on the rolled steel plate, resulting from the defect on the roll, are frequently detected at different timings in the scannings. The "1" signals indicating the presence of defects on the rolled steel plate are stored in the shift registers located at different digit positions of each shift register circuit. Consequently, it cannot be assured that all the "1" signals are transmitted to the last stage shift registers at the same time.

SUMMARY OF THE INVENTION

Accordingly, an object of the present invention is to provide a surface defect detecting apparatus which can detect a substantially periodically appearing surface defect and a randomly appearing surface defect, definitely distinguishing them one from the other.

According to one aspect of the present invention, there is provided a surface defect detecting apparatus comprising: scanning means for periodically scanning a member under inspection transferred by at least one roll in the direction of a width of the member to successively produce signals each representing a surface condition of that area of the member which is scanned in the width direction thereof; a defect signal generating circuit for producing an output signal representing the presence of a surface defect on the surface of the member under inspection in accordance with an output signal from the scanning means; a pulse generating circuit for producing a plurality of pulses in each rotation of the roll; and control means which responds to output pulses from the pulse generating circuit to sequentially write defect signals generated from the defect signal generating circuit into a memory means, reads out the data from the memory means after a predetermined amount of data is stored in the memory means, and causes a display unit to display the data read out from the memory, the data corresponding to output signals generated from the scanning means in each rotation of the roll being displayed in one of substantially parallel lines.

In the present invention, data corresponding to defect signals produced from the defect signal generating circuit in each rotation of the roll are displayed on one of substantially parallel lines. Therefore, when surface defects appear on the surface of a member to be inspected substantially in synchronism with the rotation of the roll, the data indicating the surface defects are displayed at substantially the same position on each line. Accordingly, the surface defects periodically appearing on the surface of the member under inspection are easily recognized.

BRIEF DESCRIPTION OF THE DRAWINGS

FIG. 2 is a diagram illustrating the address locations of RAM used in the surface defect detecting apparatus of FIG. 1;

FIG. 4 is an example of the display of the surface defect data displayed on a display unit in the surface defect detecting apparatus shown in FIG. 1.

DETAILED DESCRIPTION OF THE PREFERRED EMBODIMENTS

Figure 1:
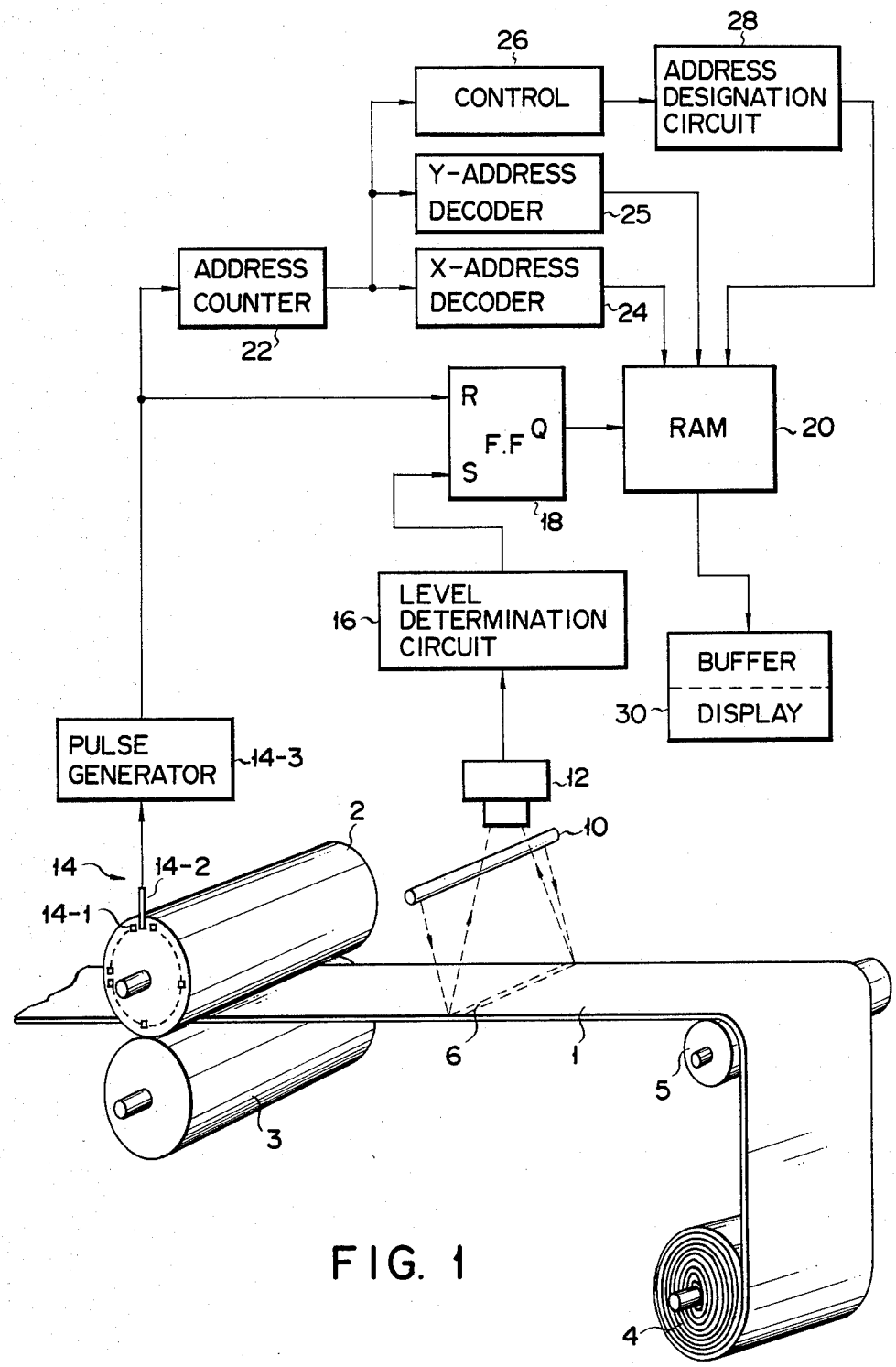
FIG. 1 illustrates in schematic and block form a surface defect detecting apparatus of an embodiment according to the present invention.

FIG. 1 shows in schematic and block form an embodiment of a surface defect detecting apparatus according to the present invention for detecting a surface condition of a steel plate 1. As well known, the steel plate 1 is rolled by a pair of rolls 2 and 3, while being pulled out. Then, the rolled steel is taken up by a take-up roll 4 via a guide roll 5. Since the rolling apparatus of this type is well known, its detail construction and the explanation relating to the construction will be omitted here.

The surface defect detecting apparatus shown in FIG. 1 includes a rod-like light source 10, such as a mercury lamp, for irradiating the rolled steel 1 over its full width, a photoelectric converting device 12 for receiving the light emitted from the light source 10 and reflected from a strip area 6 which is part of illuminated portion of the steel surface and fully covers the width of the rolled steel 1, and a rotating angle detector 14 for detecting a rotating angle of the roll 2 to generate a pulse every time the roll 2 rotates by a given angle. The rotating angle detector 14 is comprised of, for example, a series of N magnet pieces 14-1 arranged equidistantly on the outer peripheral portion of a side surface of the roll 2, a coil 14-2 disposed close to the side surface of the roll 2, which produces current every time one of the magnet pieces passes the coil, and a pulse generator 14-3 which generates a pulse when current with a value larger than a given value is produced in the coil 14-2. The photoelectric converting device 12 includes photoelectric converting elements of 2048, for example, arrayed in parallel with an axis of the rod-like light source 10, an optical device for converging light from the strip area 6 onto photosensitive surfaces of the photoelectric converting elements, and a scanning circuit which successively energizes the photoconverting elements one by one to cause the elements to produce electrical signals representing light amounts at the corresponding locations on the strip area 6. Thus, the photoelectric converting device 12 cooperates with the rod-like light source 10 to form an optical scanning device which scans the steel plate, in its width direction a plurality of times in each rotation of the roll 2. When a surface defect comes into the strip area 6, an amount of light reflected from the defective portion and received by the photoelectric converting device 12 is far smaller than that from the non-defective portions. Therefore, the photoelectric converting device 12 produces an output signal which is low in level at a time corresponding to the location of the defective portion. In this example, the optical scanning device is designed to perform N times of periodic scanning operations during each rotation of the roll 2.

The output signal from the photoelectric converting device 12 is applied to a level determination circuit 16 where the output signal is checked as to whether it contains any defect signal component or not. The level determination circuit 16 includes, for example, a differentiating circuit for differentiating the output signal from the photoelectric converting device 12, a comparing circuit for generating a "1" signal when an output signal from the differentiating circuit is lower than a predetermined value, and an AND gate circuit which receives an output signal from the comparing circuit and a high level signal generated, within each scanning period of the scanning circuit of the photoelectric converting device 12, over a shorter period than the scanning period. With this arrangement, a "1" level signal is produced from the level determination circuit 16 at a time corresponding to the location having the surface defect. An output signal of the level determination circuit 16 is coupled with a set input terminal of an R-S flip-flop circuit 18 whose reset input terminal is connected to an output terminal of the pulse generator 14-3. That is, the flip-flop circuit 18 produces a defect signal in synchronism with a pulse signal from the pulse generator 14-3 whenever one or more surface defects are detected in a scanning cycle, thus checking if there is any surface defect detected in each scanning cycle. An output terminal of the flip-flop circuit 18 is connected with a data input terminal of a random access memory (RAM) 20. The RAM 20 has a plurality of memory locations arranged in N columns and M rows as shown in FIG. 2.

The output terminal of the pulse generator 14-3 is also connected with an address counter 22 for counting output pulses from the pulse generator 14-3. An output terminal of the address counter 22 is coupled with X- and Y-address decoders 24 and 25 which supply a write address signal to the RAM 20 according to the contents of the counter 22. The X- and Y-address decoders 24 and 25 selectively designate the column and row positions of the RAM 20 according to the contents of the counter 22 in a well-known manner. Further, the output terminal of the address counter 22 is connected to a control circuit 26 which responds to an output signal generated from the counter 22 when the contents of the counter 22 reaches a predetermined value, that is, after the last write address A[MN] of the RAM 20 is designated by the address decoder 24, to trigger a read out address designating circuit 28 and supply a read out address signal to the RAM 20. All the data read out from the RAM 20 are temporarily stored in a buffer register of a display unit 30 and then displayed on the display section of the display unit 30.

The operation of the surface defect detecting apparatus shown in FIG. 1 will next be described.

Figure 3:
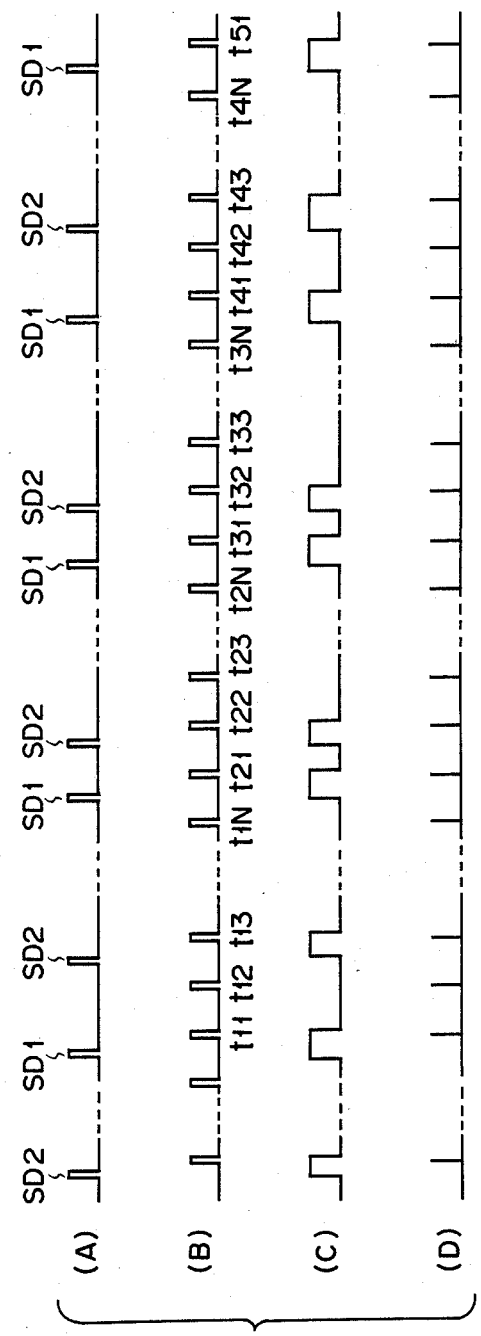
FIG. 3 shows signal waveforms for explaining the operation of the surface defect detecting apparatus shown in FIG. 1.

A member to be checked such as a steel plate rolled and pulled out by the rolls 2 and 3 is taken up by the take-up roll 4 through the guide roll 5. Part of the steel plate 1 rolled by the rolls 2 and 3 is irradiated by light from the rod-like light source 10 over its entire width. As a result, the light reflected from the illuminated strip area 6 is received by the photoelectric converting device 12. As described above, the photoelectric converting device 12 sequentially energizes photoelectric converting elements of 2048, for example, during a scanning period T1, and equivalently scans the strip area 6. After this, it stops the scanning for a stop period T2 and completes one scanning cycle in the direction of the width of the rolled steel plate 1. During the periods T1 and T2, the steel plate 1 is being transferred by the rolls 2 and 3, and now the light reflected from another strip area of the steel plate 1 is received by the photoelectric converting device 12. As in the previous scanning cycle, the photoelectric converting elements are energized successively during the scanning period T1, and the scanning is stopped during the stop period T2. In this way, the photoelectric converting device 12 scans substantially the entire surface of the rolled steel plate, and converts the light received during the scanning period into electric signals which in turn are supplied to the level determination circuit 16. The level determination circuit produces a "1" signal as shown in FIG. 3(A) when a signal indicating the presence of a surface defect on the rolled steel plate 1 is generated from the photoelectric converting device 12. In FIG. 3(A), "1" signals SD1 which substantially periodically appear indicate the surface defects caused by a defect on the roll 2, and other "1" signals SD2 are judged to indicate surface defects made on the rolled steel plate 1 by another cause.

Meanwhile, a pulse as shown in FIG. 3(B) is generated from the pulse generator 14-3 each time the roll 2 rotates by a given angle. In this embodiment, N pulses $t_{i1}$ to $t_{iN}$ are generated from the pulse generator 14-3 in each rotation of the roll 2. The interval of one rotation of the roll 2 is defined by the trailing edges of pulses $t_{(i-1)N}$ and $t_{iN}$. The flip-flop circuit 18 is reset at a trailing edge of an output pulse from the pulse generator 14-3, and set by the "1" signal from the level determination circuit 16 thereby to produce an output signal as shown in FIG. 3(C). Further, the output pulse of the pulse generator 14-3 is applied to the address counter 22. The address counter 22 counts up its count one by one in response to the leading edge of the output pulse from the pulse generator 14-3. In accordance with the contents of the counter 22, the address decoders 24 and 25 supply address signals to the RAM 20 at timings shown in FIG. 3(D), and sequentially writes data corresponding to Q output signals from the flip-flop circuit 18 in different address locations A[11], A[12], ... A[1N]; A[21], A[22], ... A[2N]; ...; and A[M1], A[M2], ... A[MN] of the RAM 20. For example, data read out from the RAM 20 at the address locations A[11] to A[1N] are transferred to the first shift register circuit, data read out from the RAM 20 at the address locations A[21] to A[2N] are transferred to the second shift register circuit, and in the same manner, data read out from the RAM 20 at the address locations A[31] to A[3N]; ...; and A[M1] to A[MN] are respectively transferred to the third to M-th shift register circuits. For example, surface defect data obtained in the first scanning cycle and indicating whether or not at least one surface defect is detected in the scanned area is written into the RAM 20 at the address location A[11], surface defect data obtained in the next scanning cycle is written at the address location A[12], and in the same way, surface defect data obtained in the N-th scanning cycle is written at the address location A[1N]. Thus, surface defect data obtained during one rotation of the roll 2 are stored in the same row of the RAM 20. Then, the defect data transmitted to the buffer register section is displayed by the display section of the display unit 30 in a known display drive manner. In this case, data group including surface defect data stored in the same row of the RAM 20 is displayed in the same line. That is, M data groups each including N surface defect data are respectively displayed on M substantially parallel lines on the display unit 30. The surface defect data may show the presence or absence of a surface defect. The defect signals are displayed in a line-by-line manner on the display unit 30.

FIG. 4 shows an example of a display of the surface defect data obtained as mentioned above. In FIG. 4, a distance D corresponds to a length of the inspected rolled steel plate 1, a distance d corresponds to a travelling interval of the steel plate 1 transferred for one rotation of the roll 2 and a width L corresponds to a length equal to N times the width of the steel plate 1. In FIG. 4, as indicated by the dot signals SD1, surface defects made on the surface of the rolled steel plate 1 by a defect of the roll 2 are substantially continuously displayed on the screen of the display unit 30. On the other hand, the surface defect on the rolled steel plate 1 owing to the other cause than the defect of the roll 2 are randomly displayed on the display unit 30, as indicated by the dot signals SD2. As described above, by the display unit 30, the surface defects caused by the defect on the roll 2 are clearly distinguished from the surface defects resulting from the other cause in a visual way, and whether any defect appears on the roll 2 or not is easily detected.

As described above, in this embodiment, surface defect data which are obtained by scanning the steel plate 1 in a width direction thereof N times during each rotation of the roll 2 are displayed in the same line. Accordingly, if there is a surface defect appearing periodically on the steel plate 1, a mark or the like indicating the surface defect is displayed at almost the same position of each display line so that the presence of such surface defect can be visually recognized without any difficulty.

While the present invention has been described by using a specific example, the present invention is not limited to the above-mentioned embodiment. In the embodiment shown in FIG. 1, the rod-like light source 10 is used, but a combination of a point light source and a rotating mirror may be used for the same purpose. In this case, with the light from the point light source, the steel plate 1 can be scanned in the direction of its width. Further, a laser beam source or an ultrasonic generating source may be used instead of the light source 10 for the same purpose.

The flip-flop circuit 18 can be omitted if the level determination circuit 16, which generates output pulses indicating a surface defect in response to an output signal from the photoelectric converting device 12, is so arranged that it generates surface defect displaying pulses with the pulse width substantially equal to a period of the output pulse signal from the pulse generator 14-3. Further, the RAM 20, the address counter 22, the address decoders 24 and 25, the control circuit 26, the address designation circuit 28 and the display unit 30 are replaced by a printer. In this case, the printer responds to the output pulse from the generator 14-3 to print dots on a printing paper when a "1" output signal is generated from the flip-flop circuit 18. The paper, as well known, is transferred a predetermined distance every rotation of the roll 2, while, a print head is returned to its initial position every rotation of the roll 2. Through this operation, the dot pattern as shown in FIG. 4 is printed.

The rotating angle detector 14 for detecting a rotating angle of the roll 2 includes the magnet pieces 14-1 and the coil 14-2. Alternately, the rotating angle detector may be constructed by using a plurality of mirror pieces, a light source and photoelectric converting elements which supply a trigger signal to the pulse generator upon receipt of the light irradiated from the light source and reflected from the mirror pieces. The rotating angle detector may also be constructed by using a disc having a plurality of slots arranged on the peripheral portion thereof and fixed to the roll shaft and a combination of a light source and the photoelectric converting elements disposed on both sides of the disc.

For brief explanation, the RAM 20 having M rows and N columns is used, but any type of RAM can be used instead of the RAM 20. For example, in practice, in order to inspect a steel plate of 1 km, 16 RAMs of TMM 314 (manufactured in Toshiba Co.) each having a memory capacity of 8 k.bit may be used. It is also possible to perform the scanning operation in synchronism with a pulse generated from the pulse generator 14-3 by, for example, supplying an output pulse from the pulse generator 14-3 to the photoelectric converting device 12.

Further, a member to be inspected may be substituted by an object other than the rolled steel plate.

What is claimed is:

1. A surface defect detecting apparatus comprising:
   scanning means for scanning a member under inspection transferred by at least one roll at a fixed period in the width direction of the member to successively produce signals representing a surface condition of the member under inspection in the width thereof;
   a defect signal generating circuit for producing output signals representing the presence or absence of surface defects on the surface of the member under inspection in accordance with the presence or absence of output signals from said scanning means;
   a pulse generating circuit for producing a plurality of output pulses with every rotation of said roll; and
   display means responding to the respective output pulses from said pulse generating circuit for displaying said output signals from said defect signal generating circuit, wherein all the output signals generated from said defect signal generating circuit during one rotation of said roll are displayed on a single line and a plurality of these lines is displayed in parallel fashion.

2. A surface defect detecting apparatus comprising:
   scanning means for periodically scanning a member under inspection transferred by at least one roll in the direction of a width of the member to successively produce first output signals each representing a surface condition of that area of the member which is scanned in one scanning cycle in the width thereof;
   a defect signal generating circuit for producing second output signals representing the presence or absence of surface defects that are detected on the surface of the member under inspection in accordance with the first output signals from said scanning means;
   a pulse generating circuit for periodically producing at least one pulse for each rotation of said roll;
   memory means for storing said second output signals stored in said memory means; and
   control means which responds to said at least one pulse from said pulse generating circuit for sequentially writing data corresponding to said second output signals generated by said defect signal generating circuit into said memory means, for sequentially reading out the stored second output signals from said memory means after a predetermined number of second output signals are stored in said memory means, and for controlling said display means to display the stored second output signals read out from said memory means, wherein the second output signals obtained during one rotation of said roll are displayed on a single line, and a plurality of these lines is displayed in a parallel fashion.

* * * * *